US012619103B2

(12) United States Patent
Portney et al.

(10) Patent No.: US 12,619,103 B2
(45) Date of Patent: May 5, 2026

(54) DIFFRACTIVE MULTIFOCAL SMALL APERTURE OPHTHALMIC LENS

(71) Applicants: Valdemar Portney, Newport Coast, CA (US); F. Richard Christ, Laguna Beach, CA (US)

(72) Inventors: Valdemar Portney, Newport Coast, CA (US); F. Richard Christ, Laguna Beach, CA (US)

( * ) Notice: Subject to any disclaimer, the term of this patent is extended or adjusted under 35 U.S.C. 154(b) by 453 days.

(21) Appl. No.: 18/191,816

(22) Filed: Mar. 28, 2023

(65) Prior Publication Data

US 2023/0314838 A1 Oct. 5, 2023

Related U.S. Application Data

(60) Provisional application No. 63/376,086, filed on Sep. 17, 2022, provisional application No. 63/371,501, (Continued)

(51) Int. Cl.
*G02C 7/02* (2006.01)
*A61F 2/14* (2006.01)
(Continued)

(52) U.S. Cl.
CPC ............. *G02C 7/041* (2013.01); *A61F 2/1451* (2015.04); *A61F 2/1618* (2013.01); *A61F 2/1627* (2013.01); *A61F 2/1654* (2013.01); *G02C 7/022* (2013.01); *G02C 7/06* (2013.01); *A61F 2240/002* (2013.01); *G02C 2202/20* (2013.01)

(58) Field of Classification Search
None
See application file for complete search history.

(56) References Cited

U.S. PATENT DOCUMENTS 4,673,406 A * 6/1987 Schlegel ............... A61F 2/1613
623/6.25
6,536,899 B1 3/2003 Fiala
(Continued)

OTHER PUBLICATIONS

Telek et al, "The Effects of Age on Pupil Diameter at Different Light Amplitudes", Beyoglu Eye Journal, vol. 3, No. 2, 2018, 80-85, DOI: 10.14744/bej.2018.43534.

*Primary Examiner* — Darryl J Collins
(74) *Attorney, Agent, or Firm* — Orbit IP, LLP; Marc G. Martino

(57) ABSTRACT
A transmissive ophthalmic lens has a first surface opposite a second surface. The first surface includes a centrally disposed diffractive multifocal zone surrounded by a peripherally disposed refractive non-multifocal zone. The second surface is a refractive non-multifocal surface. The refractive non-multifocal zone forms the far focus. The diffractive multifocal zone is no more than 2.5 millimeters in diameter to produce a far focus and an Add focus and no less than 1.5 mm in diameter for Multipeak performance. A first groove and a second groove of the diffractive multifocal zone may be the only two grooves. At least 20% of light is directed within the diffractive multifocal zone to one of the far and the Add focus. The diffractive multifocal zone may have a base curve that together with a peripheral zone is bi-sign aspheric around far focus and aspheric grooves configured for minimum spherical aberration at the Add focus.

14 Claims, 6 Drawing Sheets

Related U.S. Application Data filed on Aug. 15, 2022, provisional application No. 63/362,387, filed on Apr. 1, 2022.

(51) Int. Cl.

| | |
|---|---|
| *A61F 2/16* | (2006.01) |
| *G02C 7/04* | (2006.01) |
| *G02C 7/06* | (2006.01) |

(56) References Cited

U.S. PATENT DOCUMENTS

| | | | |
|---|---|---|---|
| 6,557,998 B2 | 5/2003 | Portney | |
| 7,073,396 B2 | 7/2006 | Hussain et al. | |
| 8,500,805 B2 | 8/2013 | Kobayashi et al. | |
| 8,610,362 B2 | 12/2013 | Seo | |
| 8,894,706 B2 | 11/2014 | Portney | |
| 10,449,039 B2 | 10/2019 | Ganesan et al. | |
| 10,517,716 B2 | 12/2019 | Luque | |
| 10,656,437 B2 | 5/2020 | Limon et al. | |
| 11,506,914 B2 | 11/2022 | Canovas Vidal et al. | |
| 2008/0030677 A1* | 2/2008 | Simpson | G02B 5/1876 351/159.44 |
| 2010/0312336 A1* | 12/2010 | Hong | A61F 2/1616 351/159.41 |
| 2011/0022170 A1* | 1/2011 | Simpson | G02C 7/042 351/159.01 |
| 2013/0201445 A1* | 8/2013 | Das | A61F 2/1618 351/159.73 |
| 2014/0168602 A1* | 6/2014 | Weeber | G02C 7/044 351/159.48 |
| 2020/0192121 A1 | 6/2020 | Anderson | |
| 2022/0287825 A1 | 9/2022 | Faria Ribeiro et al. | |
| 2022/0287826 A1 | 9/2022 | Tiwari | |

* cited by examiner

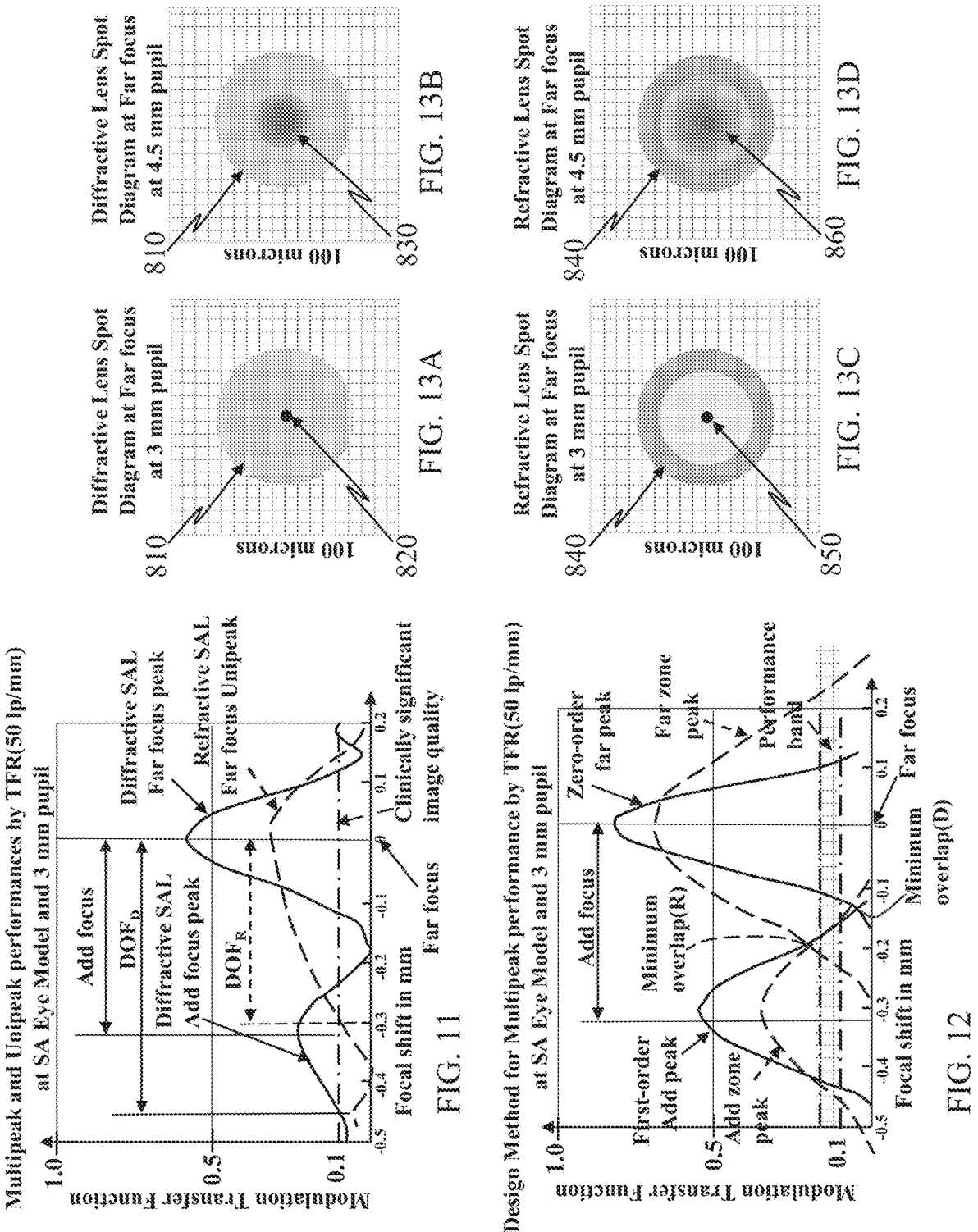

FIG. 13B

Diffractive Lens Spot Diagram at Far focus at 4.5 mm pupil

FIG. 13D

Refractive Lens Spot Diagram at Far focus at 4.5 mm pupil

FIG. 13A

Diffractive Lens Spot Diagram at Far focus at 3 mm pupil

FIG. 13C

Refractive Lens Spot Diagram at Far focus at 3 mm pupil

FIG. 11

Multipeak and Unipeak performances by TFR(50 lp/mm) at SA Eye Model and 3 mm pupil

FIG. 12

Design Method for Multipeak performance by TFR(50 lp/mm) at SA Eye Model and 3 mm pupil

DIFFRACTIVE MULTIFOCAL SMALL APERTURE OPHTHALMIC LENS

CROSS-REFERENCE TO RELATED APPLICATIONS

This utility patent application claims priority from U.S. Provisional patent applications: Ser. No. 63/362,387 filed Apr. 1, 2022, Ser. No. 63/371,501 filed Aug. 15, 2022 and Ser. No. 63/376,086 filed on Sep. 17, 2022, the entire contents of which all three applications are fully incorporated into the present application with these references.

DESCRIPTION

Field of the Invention

The present invention relates generally to a multifocal ophthalmic lens of extended depth-of-focus (DOF) performance over a monofocal lens of the same shape and material. More particularly, it relates to an extended DOF diffractive multifocal small aperture intra-ocular lens (phakic intra-ocular lens, implantable contact lens and aphakic intra-ocular lens), corneal inlay and contact lens.

Background of the Invention

Ophthalmic lenses disclosed in this application refer to phakic or aphetic intraocular lens (IOL) including implantable contact lens (ICL) that is installed inside the eye, to a corneal inlay (CI) of the eye that is installed within the eye cornea and to a contact lens (CL) that is installed over the front surface of the eye.

In describing the present invention, we shall provide the definitions of terms used. A monofocal lens is a fixed single power lens that provides good quality of vision but only within a small range of viewing distances that is usually significantly narrower than the range required from near or intermediate to far vision where far vision is usually defined at a distance of about 6 feet from the eye (around 2 meters) and beyond, near at about 2 feet (around 50 centimeters) and closer to the eye and intermediate is between far and near. Usually, it is said that a monofocal ophthalmic lens manifests a far power, far focus, and forms a far image of an object located at far distance. A monofocal lens may include a cylinder power to correct for ocular astigmatism which is referenced to in this application as non-multifocal lens; i.e., a monofocal lens that may also include cylinder.

There is a significant effort to develop a lens for presbyopia correction in a form of refractive or diffractive type lenses where image forming refractive, diffractive or their combination is placed within a lens surface within so called clear aperture. This type of the lens provides a number of powers, so called bifocal or multifocal lens. Reference to bifocal or multifocal terminology is used herein interchangeably. A multifocal ophthalmic lens can provide refractive powers, diffractive powers or a combination of both and an additional power to far power called Add power (AP), additional focus to far focus called Add focus and additional image to far image called Add image formed by an object located at a distance other than far distance. A multifocal lens may include a cylinder power to correct for ocular astigmatism and a reference to multifocal lens throughout of this application also includes a cylinder.

A multifocal ophthalmic lens includes multifocal surface to provide Add power and opposite refractive surface. The opposite surface means the refractive surface of the multifocal lens which is opposite to the multifocal surface with light passing the clear aperture of the lens through both surfaces.

A diffractive lens generally consists of a number of annular surface zones of equal area over an imaginable surface called base curve, they are called diffractive grooves or just grooves. In a simple paraxial form, the grooves, echelettes or surface-relieve profiles can be expressed by the formula $$r_j^2 = jm\lambda f,$$

the focal length (f) of m-order diffraction (m=±1, ±2, etc.) for the design wavelength ($\lambda$) can be closely approximated by the following formula:

$$f_m = \frac{r_j^2}{jm\lambda} \tag{1}$$

In the paraxial approximation the blaze material thickness of blaze shape grooves also called diffractive optical step or just step (h), produces 100% efficiency at m-order is:

$$h_m = \frac{m\lambda}{(n - n')} \tag{2}$$

Where n=refractive index of the lens material and n'=refractive index of the surrounding medium. Blaze shape is the most effective shape of diffractive multifocal lens and most used for multifocal ophthalmic lenses. Half of the step (h) in the formula (2) is used to produce bifocal diffractive lens with 40.5% of light directed to zero-order allocated to far focus and (−1)-order allocated to Add focus, i.e., m=−1. A trifocal diffractive lens manifests more complicated shape and it was described in the U.S. Pat. No. 8,500,805 by Kobayashi et al. (which is incorporated herein in full with this reference) as a superposition of two blaze surfaces where each diffractive order groove of the blaze surface of lower Add power coincides with every other groove of the blaze surface of higher Add power, $1^{st}$ order coincides with $2^{nd}$, $2^{nd}$ with $4^{th}$ and do on. Both types of lenses are commonly referred to as diffractive multifocal lenses.

If step sizes are zero or randomly sized or groove areas are randomly sized, the lens becomes a refractive type, i.e., the corresponding image locations are defined by Snell's law:

$$\frac{\text{Sin}(\phi)}{\text{Sin}(\phi')} = \frac{n'}{n} \tag{3}$$

where $\phi$=angle of incidence in surrounding medium, $\phi'$=angle of refraction in the lens material, n=refractive index of the lens material, and n'=refractive index of surrounding medium. Base curve shape of a diffractive lens is characterized by the asphericity as a combination of a spherical radius and aspheric coefficients to form an image at zero order diffraction and groves shapes and steps between the adjacent groves are characterize by phase coefficients to form an image at a certain non-zero diffractive order. A fraction of light directed to a given diffraction order is called diffraction efficiency (DE) of this diffraction order. Non-zero light is spread for multiple diffraction orders of a diffractive multifocal lens, but image viable diffractive order requires that at least 20% of total light to be directed to such diffractive order. It is called diffractive efficiency (DE) of the diffractive order. A non-zero diffractive order with sufficient DE is then called Add focus and a difference between Add focus and zero diffractive order focus also with sufficient DE is called Add power if the distance is specified in diopters or focal shift if the distance is specified, say, in millimeters.

Image forming area of a lens with defined optical specifications is called clear aperture (CA). In case of a monofocal ophthalmic lens, there is a clear aperture to form far image but in case of a multifocal ophthalmic lens, it might include several different clear apertures, one is to form far focus and called $CA_F$ and another ($CA_A$) to form an Add focus in addition to far focus. In addition, eye pupil serves as a clear aperture ($CA_Y$) of the eye optical system. There are a number of publications on a pupil diameter at different light conditions, for instance, a paper by HH Telec et al. on the effect of age and lighting on pupil diameter that was published in Beyoglu Eye J, 2018; 3(2), 80-85; DOI: 10.14744/bej.2018.43534. It confirmed the validity of a nominal pupil at daytime (photopic) condition to manifest diameter $CA_{YP}$=3.0 mm which is reduced for mature population (>60 year of age) by almost 0.5 mm, to $CA'_{YP}$=2.5 mm. The eye pupil increases in low light condition, so called mesopic condition and, as a standard, $CA_{YM}$=4.5 mm diameter is used in optical testing to emulate pupil diameter at mesopic condition. Thus, a multifocal ophthalmic lens of an eye optical system leads to two different states: (1) $CA_A$>$CA_{YP}$ in a daytime (photopic) condition, and a corresponding multifocal lens is called "full aperture lens" or FAL, and (2) $CA_A$≤$CA'_{YP}$ in daytime condition, and the corresponding multifocal lens is called "small aperture lens" or SAL. Thus, a multifocal lens with $SA_A$≤2.5 mm is defined as a small aperture lens regardless of age. Often, full aperture lens manifests $CA_A$>$CA_{YM}$=4.5 mm to cover mesopic condition.

Thus, refractive multifocal lens specifications are characterized by foci distribution defined by Snell's law, diffractive multifocal lens specifications are characterized by foci distribution defined by base curve curvature for zero order diffraction and phase coefficients for a non-zero order diffraction. There are different types of refractive-diffractive multifocal designs. A refractive-diffractive multifocal lens might be a zonal design where there is a zone of refractive characterization and zone of diffractive characterization. An example is described in U.S. Pat. No. 7,073,396 by Portney, which is incorporated herein in full with this reference. Another option of refractive-diffractive design is to include a base curve with multifocal characteristic as a refractive multifocal characterization defined by Snell's law (this is the reason that zero-order diffractive focus or power is often called refractive focus or power of a diffractive lens) and a non-zero diffraction order provides additional multifocal specification. An example is described in U.S. Pat. No. 8,610,362 by Portney, which is incorporated herein in full with this reference. Another option of refractive-diffractive multifocal optic was introduced in U.S. Pat. No. 6,536,899 by Fiala (which is incorporated herein in full with this reference) where each diffractive step between the diffractive grooves is replaced by refractive sub-zone of a power coinciding with one of the diffractive powers leaving the remainders of the original diffractive grooves to maintain diffractive specifications.

The other complementary to Add power (AP) term used is depth-of-focus (DOF). DOF refers to a range of acceptable image quality set by a specific clinically significant image quality. For instance, clinically a DOF is commonly defined by a range of vision in diopters that is no less than 20/40 visual acuity (VA) per Snellen Chart. In-vitro lab testing, DOF is commonly defined as an image range in diopters or focal shift in millimeters that manifest at least 0.1 of Modulation Transfer Function (MTF) for a selected spatial frequency in line pair per millimeter (lp/mm) and the corresponding test characterization is called Through Focus Response (TFR) at certain spatial frequency. A TFR testing is commonly conducted in Eye Model and 50 lp/mm of spatial frequency is used as a representation of 20/40 VA clinically. Add Power (AP) on the other hand, can be defined for multifocal ophthalmic lenses with discrete foci like bifocal or trifocal manifesting Multipeak performance in terms of TFR. AP is a measure of distance in diopters from a peak image at an Add focus to far focus. If a multifocal ophthalmic lens represents continuous foci range by so called Unipeak performance in terms of TFR without discrete peaks of images, DOF and AP are used interchangeably as they represent equivalent measures for a range of vision in an Unipeak performance. Thus, DOF is a more general term over AP and a monofocal lens also manifest DOF>0 (about 0.5 D clinically) even if its AP=0 due the absence of Add power. Both terms AP and DOF are used interchangeably in this application unless each is specifically differentiated as a specific measure of an ophthalmic lens imaging characteristic.

The initial focus of the presbyopia correction has been to develop FAL type refractive and diffractive ophthalmic lenses to provide effective Add powers, initially only at near focus, so called bifocals, and later at near and intermediate foci, so called trifocals. Such multifocal ophthalmic lenses have achieved excellent image efficacy particularly in a form of IOLs, but the downside was that some patients experienced undesirable visual effects called dysphotopsia in a form of a bright artifact of light such as arcs, streaks, starbursts and rings, jointly termed as halos. Dysphotopsia is specific to far vision phenomenon observed at low light conditions particularly when viewing bright objects at dark background (streetlights, car lights and so on) or in a form of shadows at high contrast transitions at viewing objects (edges of a building, edges of tree trunk and branches against a light background and so on). Most patients tolerate halos with IOLs and lesser degree with CLs, but many discontinue the use of multifocal CL particularly by with higher Add power or require lens exchange in case of multifocal IOLs.

More recently the focus of multifocal ophthalmic IOL development for presbyopia correction has shifted to the issue of halos and many innovations have appeared in recent years. The effort was also combined with a reduction of the range of vision from far to intermediate as a new class of IOLs as the improvement over monofocal IOLs. The corresponding IOLs are called extended depth-of-focus IOL or EDOF IOL for short. For a convenience, the term EDOF lens has been expanded in this patent application to contact lenses and inlays as well as to any range of vision with the same objective to mitigate the halos.

A development of an EDOF ophthalmic lens has been a subject of many innovations and their review is needed in order to recognize the uniqueness of the present discovery. The requirements for EDOF ophthalmic lenses in replacing monofocal ophthalmic lenses can be distilled into tree points: (1) a substantive reduction of halos to a level similar with monofocal lenses, (2) effective increase of DOF over monofocal lenses by at least 1 D, i.e., DOF≥1.5 D, and (3) providing a comparable to monofocal image quality of far vision at different lighting conditions. Meeting all three objectives will allow the effective replacement of monofocal ophthalmic lenses and they are served as a matrix to analyze the prior art and the present invention.

One approach to reduce halos has been described in U.S. Pat. No. 10,656,437 by Limon et al. (which is incorporated herein in full with this reference) with diffractive (phase) pattern to increase DOF at each near and far and reducing size of halos by 25%. The principle used was similar to one in the U.S. Pat. No. 6,557,998 by Portney (which is incorporated herein in full with this reference) for refractive multifocal optic to increase DOF at each near and far. Such design approach to create image continuity between far and near showed only a quite modest effect on a halo reduction.

Another approach was to reduce Add power to a smaller range of far to intermediate while maintaining FAL diffractive characteristic which was commercially apply in Tecnis Symfony IOL (Johnson & Johnson) and AT LARA 829MP (Zeiss). The approach has not resolved the issue of halos.

More lately, the attention has shifted to the ophthalmic lenses with SAL characteristic of multifocal refractive designs. Corresponding refractive multifocal designs with elevated power at central zone have been described in U.S. Pat. No. 11,506,914 by Canovas et al., which is incorporated herein in full with this reference (most elevated power was close to the center of the lens). Refractive IOLs with extended DOF which include central zones of variable curvature has been also described in U.S. Pat. Appl. No: 2022/0287825 by Ribiero et al. and U.S. Pat. Appl. No: 2022/0287826 by Tiwari, both of which are incorporated herein in full with these references. EDOF IOL lenses based on the corresponding approach were commercially released: Acrysof IQ Vivity IOL (Alcon), Tecnis Eyhance IOL (Johnson & Johnson) and LuxSmart Crystal (Bausch & Lomb). The design approach involves refractive multifocal profiles of elevated power at a small central area of the lens below 2.5 mm diameter. It largely resolved the issue of halos and far image quality at different lighting conditions but resulted only in a limited DOF as clinically demonstrated by the commercially available EDOF IOLs—only about 0.5 D increase over monofocal lens. Thus, the approach to use refractive multifocal SAL was lacking an effective DOF increase over a monofocal lens.

A pinhole principle (small aperture effect) was also suggested for as a principle of EDOF lens design—a small diameter is created by a mask to increase DOF. It has been described in U.S. Pat. No. 10,449,039 by Cristie et al. U.S. Pat. Appl. No: 2020/0192121 by Anderson (which is incorporated herein in full with this reference) included pigmented ring at corneal inlay or contact lens to create small aperture effect of increased DOF. A commercial EDOF IOL based on the pinhole principle was developed as AcuFocus IC-8 IOL (Bausch & Lomb). Although the approach managed halos, nevertheless, DOF increase over corresponding monofocal lens was limited to about 0.5 D and, in addition, image quality became restricted by opaque mask presence due to the loss of light adjustment with eye pupil increase at low light conditions. Multiple studies have shown that the visual acuity reduces from photopic, i.e., daytime condition (around 100 cd/m²) to mesopic, i.e., twilight condition (around 1 cd/m²) by several visual acuity lines, thus creating a safety issue with the used of light blocking mask in mesopic condition. Due to such limitation, AcuFocus IC-8 IIOL was prescribed only for unilateral implantation to allow the fellow eye to compensate lens restriction in image quality at a lower light (mesopic) condition. This results in a potential loss of binocularity. Binocularity is important factor in improving vision with its ability to improve visual acuity up by a factor of √2 over the unilateral acuity.

Thus, a purely pinhole approach has manifested a limited DOF increase over monofocal lens and U.S. Pat. No. 10,517,716 by Luque (which is incorporated herein in full with this reference) describes an intraocular lens with a surface with opaque mask having a small zone of a multifocal refractive or diffractive profile for additional DOF expansion over the DOF extension produced by a small aperture effect. Though Luque mentioned a diffractive design option at such small zone within the opaque mask, he doesn't provide any specific of the design or grooves exposure within the central mask opening. He actually stated the preference for the refractive design because the pupil independence principal advantage of the diffractive surface over refractive optic does not exist for small aperture lens created by mask application and light directed to high diffraction orders may cause halos. It will be shown in this application of the present invention that the refractive multifocal design has very limited benefit to increase DOF in small aperture lens and resulted in lower image quality as compared with the present invention. In addition, the presence of a mask in refractive or diffractive multifocal design limits image quality at low light condition and would likely be suitable only for unilateral use similar to the experience with AcuFocus IC-8 IOL. The present invention will demonstrate that the extended DOF can be achieved without a mask as well as the exceptional far image quality without sacrificing the need to limit halos.

In summary, all prior art references and corresponding clinical products to manage halos have not achieved other necessary objectives to replace monofocal ophthalmic lens, such as to sufficiently extend DOF over the monofocal lens and achieve far image quality to a level of monofocal lenses at different light conditions. The present invention offers the lens design and method that resolve the conflict between above objectives (halo reduction, DOF extension and high far image quality) as manifested by commercial products and the prior art. The described design ophthalmic lens can be applied to any ophthalmic lens application that involves presbyopia correction for successful replacement of monofocal ophthalmic lenses for further extension of patient's benefits in meeting their visual needs.

SUMMARY OF THE INVENTION

An ophthalmic lens in accordance with the present invention consists of front and back surfaces. The lens includes a central diffractive multifocal zone no more than 2.5 mm diameter which defines the lens as a diffractive multifocal (DM) small aperture lens (SAL). Such limit of a multifocal zone size was determined to mitigate halos produced by a multifocal ophthalmic lens. The diffractive optic has been used so far only for full aperture lenses, i.e., at least 4 mm diameter diffractive multifocal zone because of diffractive multifocal central benefit to be able to split light at certain ratio regardless of the eye's pupil. It means if light is split, say 50/50 between far and Add foci, the same light split is maintained for 2.5 mm pupil or 5 mm pupil to ensure the image quality at each focus for different pupil sizes. No one skilled in the art has seen before or anticipated the benefit of a diffractive multifocal optic for small aperture application. The unexpected outcome of the present invention was that a lens with diffractive multifocal zone of 2.5 mm diameter or less is superior to a refractive multifocal small aperture lens of 2.5 mm diameter or less due to its ability to provide a multipeak performance for superior image quality at far focus and extended DOF with similar reduction in halos. In addition, in order to ensure the multipeak performance of a diffractive multifocal small aperture lens per the present invention, it was also desirable for the diffractive multigoal zone to be no less than 1.5 mm diameter. Thus, the invention described in the present application wasn't obvious for the inventors and for other persons skilled in the art that an ophthalmic lens with a diffractive multifocal zone within 1.5 mm and 2.5 mm diameters provides superior performance over a refractive multifocal small aperture in terms of more extended depth-of-focus and excellent image quality a far and an Add foci as the result the multipeak performance as compared with unipeak performance produced by the refractive multifocal small aperture lens. Prior art (U.S. Pat. No. 10,517,716 by Lugue, for instance) actually discounted the use of a diffractive multifocal lens for small aperture appliocation.

The central zone to manifest Add power by the diffractive multifocal design and encompass two full circular diffractive grooves. Central diffractive multifocal zone is to create Add focus at higher diffraction order and far focus at zero diffraction order produced by virtual base curve of the diffractive multifocal ophthalmic lens where at least 20% of light is directed to each focus. Only such diffractive foci form images and are referred to as diffractive foci in the present invention. The peripheral zone outside the central diffractive multifocal zone is transparent refractive non-multifocal surface to produce far focus. It is adjoining to the central diffractive multifocal zone. Base curve of the central diffractive multifocal zone or the opposite surface is non-multifocal surface which can be spherical, aspheric, and toric. The corresponding diffractive multifocal small aperture ophthalmic lens is abbreviated as DM SAL.

In the prefer embodiment of the present invention the base curve of the central diffractive zone continuous to the refractive peripheral zone to form together a surface shape to produce far focus at different aperture sizes up to about 8 mm diameter. Such surface shape can be spherical or aspheric including bi-sign aspheric as described in the U.S. Pat. No. 8,894,706 by Portney, which is incorporated in full herein with this reference.

In another embodiment of the present invention the central diffractive multifocal zone radius coincides with the outside radius of the second (peripheral) circular groove of the central diffractive multifocal zone.

Still in another embodiment of the present invention the sag of the peripheral refractive zone at its internal diameter considers with the sag of the diffractive multifocal zone at their junction to avoid surface step in the transition between central diffractive multifocal zone and peripheral refractive zone.

In another embodiment of the present invention, the diffractive multifocal small aperture lens provides Add power of smaller magnitude and Extra Add power of larger magnitude. Such lens is called diffractive trifocal small aperture lens. The diffractive trifocal surface periodicity is a superposition of periodicity of larger groves and periodicity of smaller grooves which are synchronized to have 2 smaller grooves to coincide with 1 larger groove. The periodicity of larger grooves is responsible for smaller Add power and the central diffractive multifocal small aperture zone is sized to encompass two such grooves. The periodicity of smaller grooves is responsible for larger Extra Add Power and the central diffractive multifocal small aperture zone encompasses four such grooves.

In preferred embodiment of the current invention, the Add power of diffractive multifocal small aperture lens lies within 1.0 D and 2.5 D at spectacle plane to provide continue range of image quality within the range from far power to Add power that is close or above the minimum clinically significant image quality for in-vitro testing by modulation transfer function (MTF) at spatial frequency of 50 lp/mm which is analogous to 20/40 visual acuity of Snellen Chart. The minimum clinically significant image quality is set at MTF(50 lp/mm)=0.1.

The present invention also includes diffractive multifocal surface construction that converts an optical step between the adjacent grooves into multiple sub-steps with a refractive segment between the adjacent sub-steps. A segment between the sub-steps is shaped to refract light to one of the diffractive foci of the diffractive multifocal zone. The construction of alternating sub-step and refractive segment is to reduce optical step into small sub-steps that minimizes light scattering at a transition between the grooves and produce a smoothened optical transition between the grooves to avoid a damage to the adjacent ocular tissue by the diffractive surface—cornea by back diffractive surface of a diffractive contact lens, stroma by diffractive corneal inlay, crystalline lens by back diffractive surface of implantable contact lens (ICL). The conversion of optical step into a set of sub-steps and refractive segment is independent of the grooves shape, base curve and diffractive surface groove periodicity and only dependent on step height and chosen smallest size of the sub-step that minimizes light scattering and smoothened the diffractive surface.

The present invention also describes a method to guide the design of a multifocal small aperture ophthalmic lens (can be applied to any multifocal lens) to manifest Unipeak or Multipeak performance in terms of Through Focus Responses (TFR) at selected clinically significant image quality. The visual acuity of 20/40 line of Snellen chart is a most common clinically significant image quality measure in clinical testing which corresponds to clinically significant image quality of MTF=0.1 at 50 lp/mm in in-vitro lens testing at the nominal eye model. The method is to guide multifocal lens configuration in selecting multifocal zone diameter, Add power magnitude and optical design of the multifocal ophthalmic lens to provide preferable Multipeak performance characterized with Add power as a separation between image peaks. A small aperture lens (SAL) design with Multipeak performance allows to elevate image quality at discrete optical powers placed at far focus and Add focus and increase DOF at the expense of image quality reduction between the image peaks which can still meet clinically significant image quality to provide continuous DOF. Clinically significant image quality in the design method is defined as MTF(50 lp/mm)=0.1. The method demonstrates the limitation of a design with Unipeak performance in terms of reduced DOF range and lower far image quality and which is commonly manifested by refractive small aperture lenses. The preferred SAL design per the present invention manifests Multipeak performance with the Add power of 1.75±0.5 D that provides minimum image quality between the image peaks in photopic condition that is close (within 10%) of the clinically significant image quality of MTF(50 lp/mm)=0.1 to achieve a continuous DOF.

The specifications of the present invention will demonstrate and explain the advantage of diffractive multifocal small aperture ophthalmic lens design over the refractive small aperture design due to fundamental characteristic of the diffractive optic as the combination of two virtual lenses of equivalent clear apertures. Each virtual lens can be independently specified; one as a refractive lens defined by the base curve shape with its imaging characteristics determined by Snell's law, and another as a diffractive lens specified by the periodic structure of diffractive surface grooves with its imaging characteristics determined by phase coefficients. It has been commonly recognized that diffractive ophthalmic lens is beneficial over refractive lens for a full aperture lens application due to pupil independence principle—light distribution between foci and, therefore, image quality is maintained at different pupil sizes. The unexpected discovery of the present invention is that the diffractive ophthalmic lens is also beneficial over refractive lens for small aperture lens application as well by providing Mutipeak performance due equivalence in clear apertures of its virtual refractive and diffractive lenses. Multipeak performance by diffractive multifocal small aperture lens per the present invention allows not only a significant halo reduction but extended Depth-of-Focus and high far image quality at different light conditions over the prior art lenses. The diffractive multifocal small aperture lens per the present invention meets the requirements needed for a successful replacement of monofocal lenses to expand vision quality of the patients over the present-day product offering.

BRIEF DESCRIPTION OF THE DRAWINGS

The accompanying drawings illustrate the invention. In such drawings:

FIG. 11 demonstrates theoretical TFRs ay 50 lp/mm in SA Eye Model and 3 mm aperture of the diffractive multifocal EDOF IVB IOL per the present invention and analogous to it in terms of light split between far, central zone size and 1.75 D Add power refractive multifocal small aperture IOL of the prior art. The comparison is to demonstrate superiority of Multipeak performance of the diffractive multifocal SAL over Unipeak performance by refractive multifocal SAL in terms of expanded range of DOF and far image quality.

FIG. 12 illustrates a design method per the present invention to construct a multifocal lens to manifest Multipeak performance. The method is to guide a selection of central multifocal zone size, Add power and optical design of lens surfaces.

FIGS. 13A through 13D are to compare out-of-focus far blurs which are origin of halos between diffractive multifocal small aperture IOL (EDOF IVB IOL) and analogues to it refractive multifocal small aperture IOL referenced to on FIG. 11. The overall sizes of the blurs are equivalent between two small aperture designs though light distributions within the blurs are different which reflects a difference between diffractive and refractive multifocal principles. The light distribution comparison supports the advantage of the diffractive multifocal SAL over refractive multifocal SAL.

DETAILED DESCRIPTION OF THE PREFERRED EMBODIMENTS

Figures 1, 2:
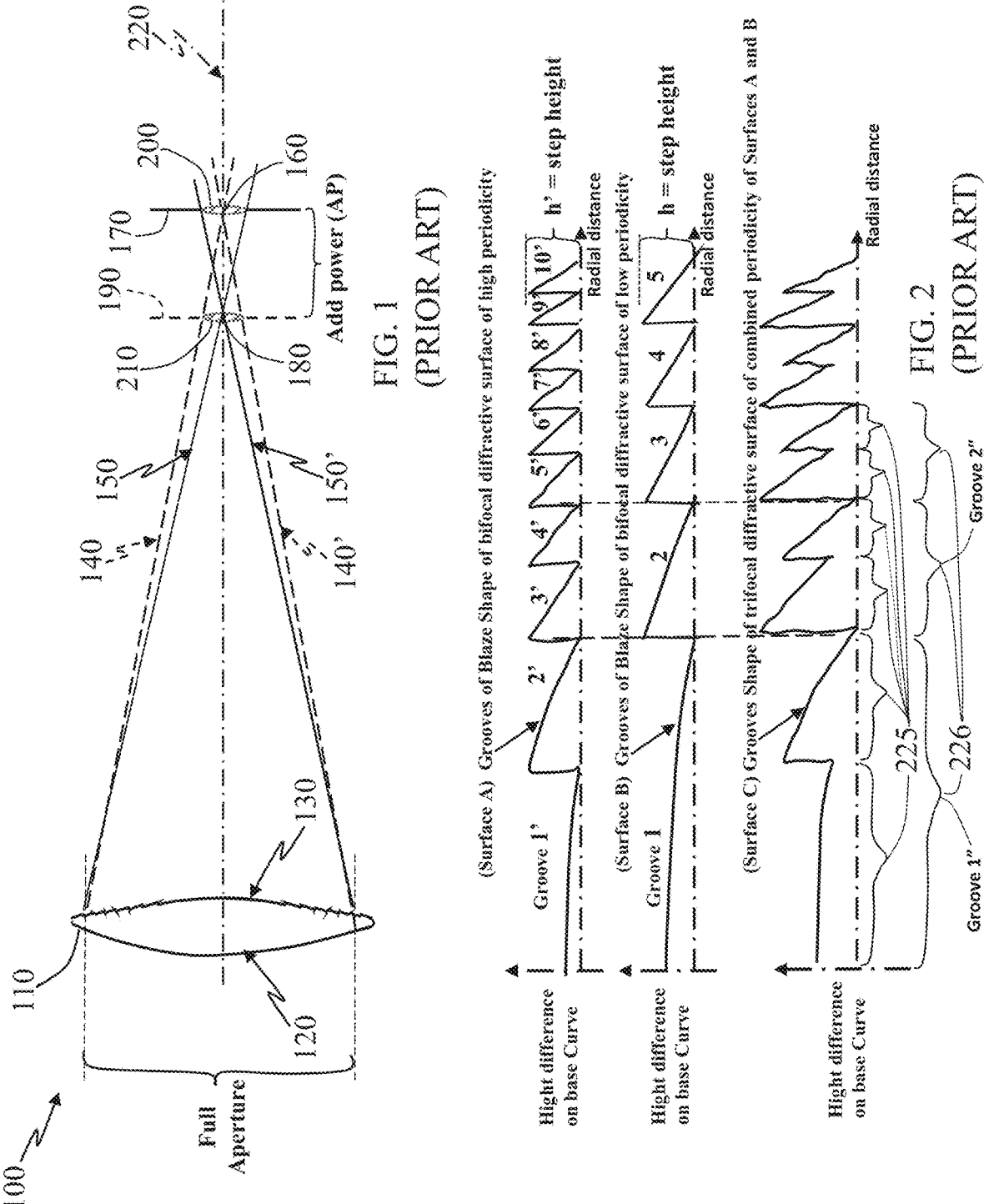
FIG. 1 demonstrates prior art full aperture diffractive multifocal lens with two diffractive foci and out-of-focus blur at each focus. Out-of-focus blur at far focus formed by out-of-focus image at Add focus is the origin of halos in multifocal optic.
FIG. 2 illustrates a definition of grooves in case of trifocal diffractive lens which is the superposition of blaze shapes of synchronized diffractive bifocal surfaces that creates surface structures of low and high periodicities that are equivalent to periodicities of grooves of the synchronized diffractive bifocal surfaces.

FIG. 1 demonstrates a prior art full aperture diffractive multifocal lens 100 where full aperture is clear aperture of a multifocal back surface 130 that occupies almost all the lens surface leaving out only a small periphery 110 outside the clear aperture. The lens 100 includes front refractive surface 120. The lens 100 forms two diffractive foci; a far focus 160 at optical axis 220 at retinal plane 170 and an Add focus 180 at optical axis 220 at Add image plane 190 located at Add power distance from the retinal plane 170. Peripheral rays 140 and 140' pass through the focus 160 to form an out-of-focus blur 210 at Add image plant 190. Peripheral rays 150 and 150' pass through the Add focus 180 to form an out-of-focus far blur 200 at the retinal plane 170. The blur 200 at far focus is the origin of halos which occurs at far vision and as such, its size and light intensity determine how disturbing a halo might be for a patient. According to ray tracing geometry shown, the blur at the far depends upon size of the zone forming Add focus and Add power magnitude—larger zone size leads to larger blur and larger Add power leads to larger blur.

FIG. 2 illustrates a trifocal diffractive shape as a superposition of two blaze shapes of diffractive bifocal surfaces without base curve contributions and referenced to as a blaze shape of a bifocal diffractive surface of high periodicity as (Surface A) with 10 grooves shown (Groove 1' and so on), blaze shape of a bifocal diffractive surface of low periodicity as (Surface B) with 5 grooves shown (Grooves 1 and so on) and surface shape of trifocal diffractive lens without base curve contribution as a structure 226 of low periodicity equaled to low periodicity of the grooves of the Surface B and structure 225 of high periodicity equaled to high periodicity of the grooves of the Surface A and is referenced to as Surface C. A grooves periodicity is defined in a bifocal lens by periodic widths of the grooves as shown in Surface A and Surface B and a structure periodicity is defined in a trifocal lens by periodic widths of each structure 225 or 226 as shown in Surface C. A trifocal diffractive lens manifests more complicated shape than bifocal diffractive lens defined by the structures of high and low periodicities and is described in the U.S. Pat. No. 8,500,805 by Kobayashi et al. (which is incorporated herein in full with this reference) as a superposition of two blaze bifocal surfaces where each diffractive groove of the blaze surface (B) of low periodicity coincides with every other groove of the blaze surface (A) of high periodicity, i.e., width of groove 1 of surface (B) coincides with the combined widths of grooves 1' and 2' of surface (A), width of groove 2 coincides with combined widths of grooves 3' and 4' and so on. It is called that the blaze surfaces (A) and (B) are synchronized to form trifocal surface (C) of the structures of the same periodicities. Equivalently to grooves synchronization between Surface A and Surface B, the high and low structures 225 and 226 are also synchronized in the trifocal surface (C). The low periodicity is responsible for Low Add power (AP) of the trifocal surface (C) and high periodicity is responsible for High Add power (AP') of the trifocal surface (C). Commonly, the periodicity of grooves is selected for AP' to provide near focus (around 3 D Add) and then AP provides an intermediate focus (around 1.5 D Add).

As an example, in case of IOL, if the low periodicity structure of surface (C) forms AP=1.75 D in IOL plane, then the synchronized high frequency structure of surface (C) would produce AP'≈3.00 D in IOL plane. Per the definition of the present patent application, the grooves of trifocal surface (C) are defined as the low periodicity structure that is equivalent in corresponding widths of the low periodicity grooves of the surface (B). Thus, diffractive trifocal small aperture lens has central multifocal zone constructed with at least Groove 1" and Groove 2" of the periodicity coinciding with grooves 1 and 2 of the blaze diffractive shape of low periodicity. If only 2 structure widths of low periodicity, i.e., Groove 1" and Groove 2", used within 2.5 mm diameter of diffractive multifocal zone, then 4 structure widths of high periodicity structure (2 structure widths per each Groove 1" and Groove 2") are also included within the multifocal zone. If a larger number of low periodicity structure fit within 2.5 mm multifocal zone diameter, then a double number of high periodicity structure widths (2 high periodicity structure widths per each low periodicity structure width) are included to form diffractive trifocal small aperture lens.

Figures 3, 4:
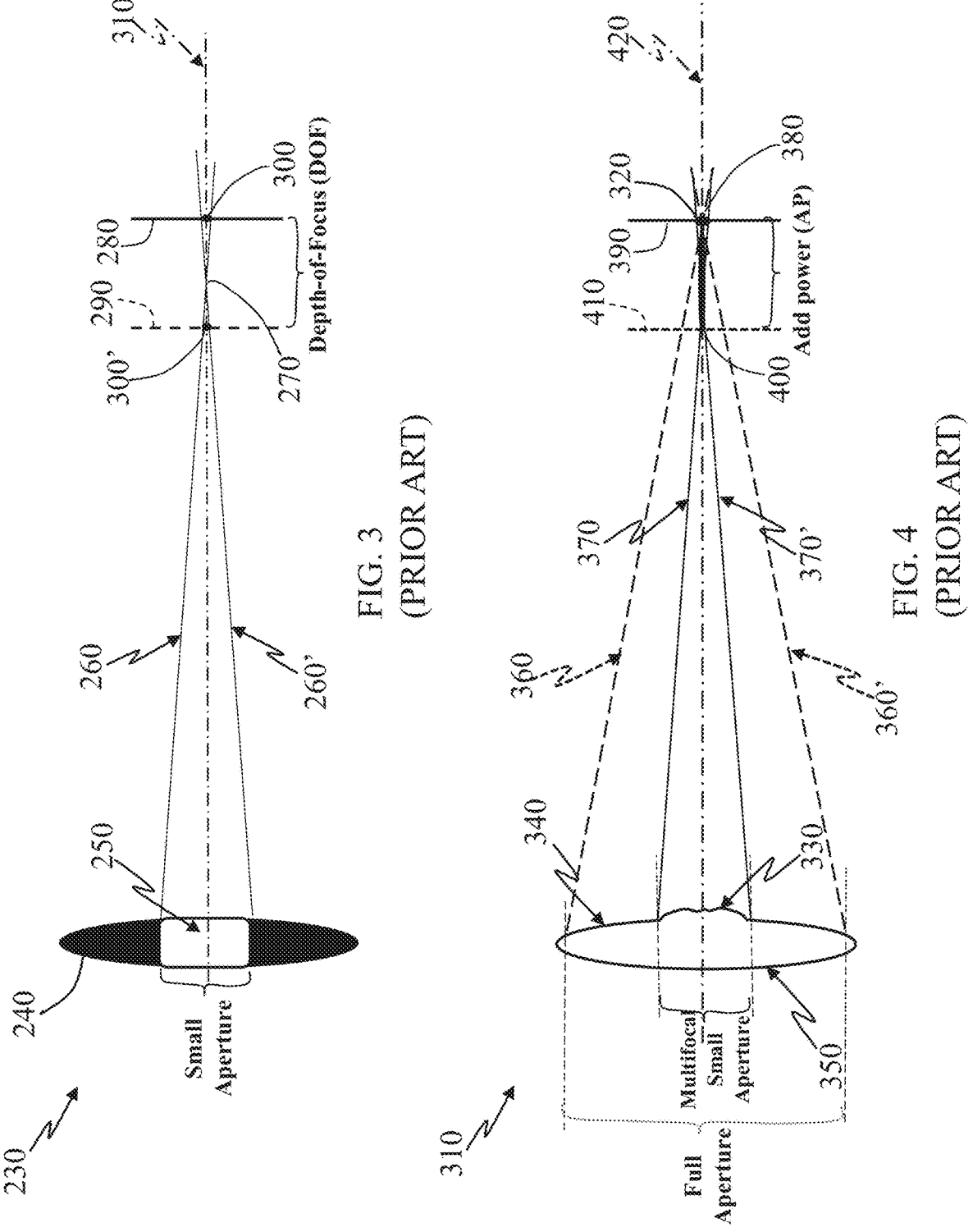
FIG. 3 demonstrates prior art small aperture lens based upon pinhole principle as one of the options to expand DOF and reduce out-of-focus blur at far image to reduce halos at the expanse of image quality at mesopic condition.
FIG. 4 demonstrates prior art refractive multifocal small aperture lens with central refractive multifocal zone designed to reduce out-of-focus blur at far focus thus reducing halos. Construction and asphericity of the refractive surface at central multifocal refractive zone are used to produce progressive, zonal or their combination of refractive powers to extend DOF over the corresponding monofocal lens but with a limited outcome.

FIG. 3 demonstrates prior art small aperture lens 230 based upon pinhole principle as one of the options to reduce out-of-focus blur at far image thus to reduce halos. The central small aperture 250 of the lens 230 is transparent to form focus 270 at the optical axis 310 as shown by the peripheral rays 260 and 260'. The part 240 of the lens 230 outside aperture 250 is opaque by different means, mask, or non-transparent material. The blur 300 at the retinal plane 280 is defined by a clinical image quality which is commonly set as 20/40 of Snellen chart and DOF is defined by a distance between plane 290 where the blur 300' is at image quality reaching clinical image quality, say 20/40 of visual acuity. A comparison of the blur 300 of FIG. 3 with blur 200 of FIG. 1 for DOF of FIG. 3 equals AP of FIG. 1, demonstrates a significant reduction in blur size at retail planes for the lens operating by pinhole principle as compared with full aperture lens; a blur size is proportional to the size of clear aperture 250.

The issue with pinhole lenses is a reduction of the amount of light passing through the lens resulted in image quality reduction particularly at low light condition (mesopic conditions) because retinal response is highly dependent upon the amount of light reaching the retina. As a compromise, a clear aperture of ophthalmic lens can be selected to pass enough light for operation in a daytime (photopic) condition which allows to increase DOF over a monofocal lens by at least 0.5 D and still manage halos, but such lens use is limited to unilateral application with fellow eye helping vision in mesopic condition.

FIG. 4 demonstrates prior art refractive small aperture lens 310 with central refractive multifocal zone 330 to expand DOF and reduce blur 320 at far focus 380 at retinal plane 390 in order to reduce halos. The opposite surface 350 is a refractive surface as well as peripheral zone 340 to form far focus. The lens 310 tradeoff pinhole principle of lens 230 to increase DOF for the increase in the amount light by including multifocal refractive surface 330 within lens small aperture and transparent refractive peripheral zone 340 outside the small central zone. In this case we have a full aperture lens to form far focus 380 and a small aperture lens to form Add focus 400 at Add plane 410. The peripheral rays 360 and 360' of the full aperture form far focus 380 at the retinal plane 390 and the peripheral rays 370 and 370' of the multifocal small aperture may intersect optical axis 420 within the range of Add power, i.e., from far focus 380 to Add focus 400, though to be effective in expanding DOF of lens 310, the rays 370 and 370' shall be close to Add focus 400. Asphericity of the refractive surface at central multifocal zone 330 can be to produce (1) progressive power change—power continually changes from far focus, say, at the lens center to Add focus at multifocal small aperture periphery, (2) zonal power change—multifocal zone 330 consists of zones of far and Add powers, say, centrals zone of far power and peripheral zone of Add power, or (3) a combination of progressive and zonal designs within the central multifocal zone 330 to extend DOF over the corresponding monofocal lens. Small aperture size 330 presents a challenge for progressive power design because it limits the area associated with, say, 0.25 D increment and, therefore, the amount of light directed to each increment of power within Add power range. To be effective to form the image, it takes at least 20% of light at each increment thus limiting the Add power range due to small multifocal zone diameter—it takes 5 increments of 0.25 D to provide 20% of light at each increment. Zonal design also results in limited DOF as will be shown in FIG. 11. A combination of progressive and zonal design is not expected an improvement in DOF either. The analysis has been supported by the clinical trials with commercial products in case of IOLs—clinical data of refractive SAL such as Vivity, Eyhance. LuxSmart Crystal IOLs support about 0.5 D DOF increase over a monofocal IOL, i.e., they provide about 1 D of DOF.

Figure 5:
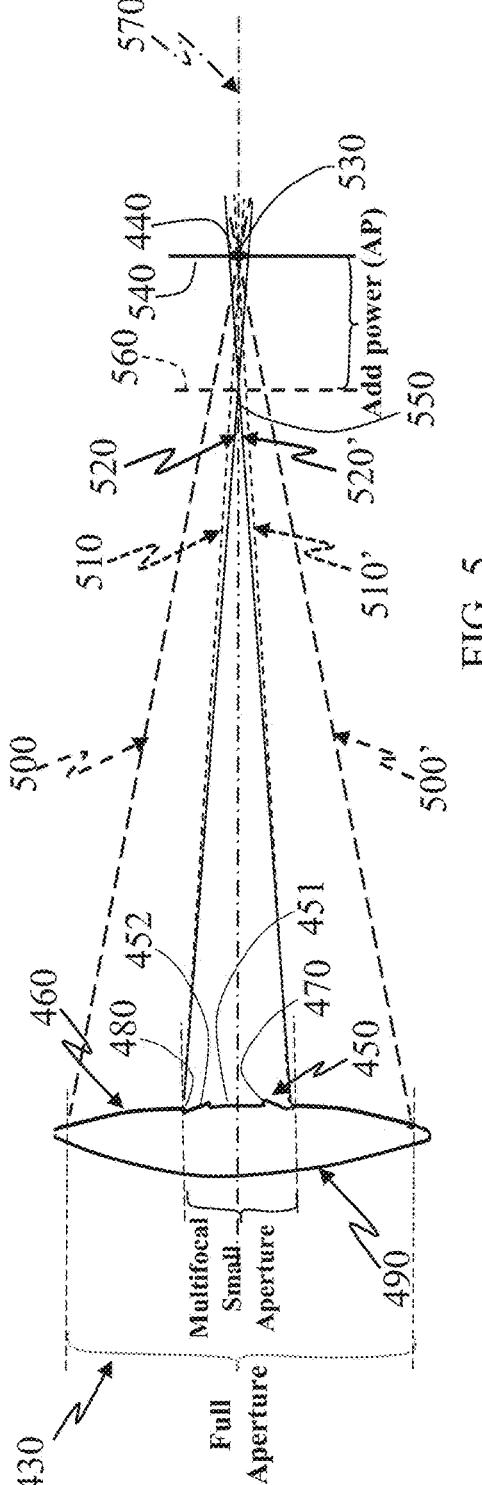
FIG. 5 demonstrates diffractive multifocal small aperture lens per the present invention with central diffractive zone consisting of two grooves to form two diffractive foci. Zero order diffraction is allocated to far focus and $1^{st}$ order diffractive to Add focus. It has been an unexpected outcome that the diffractive multifocal small aperture lens per the present invention demonstrates significant improvement in DOF and far image quality over refractive multifocal small aperture lens with similarly reduced of out-of-focus blur size from full aperture multifocal lens.

FIG. 5 demonstrates a diffractive multifocal small aperture lens (DM SAL) 430 of the present invention with a central diffractive multifocal zone 450 consisting of two grooves (Groove 1 being element 451 and Groove 2 being element 452) with central step 470 between the grooves and peripheral step 480 between the groove 2 and peripheral refractive zone 460. The grooves are to form two foci, far focus 530 at retinal plane 540 and Add focus 550 at the add plane 560 of Add power from the retinal plane 540. The opposite surface 490 of the lens 430 is non-multifocal refractive surface, i.e., spherical aspheric or toric. The peripheral rays 500 and 500' of the full aperture that encompasses the peripheral zone 460, form far focus 530 at crossing with optical axis 570. The same with peripheral rays 510 and 510' of the multifocal small aperture 450 to form far focus 530 by coinciding with diffractive focus of zero order diffraction and peripheral rays 520 and 520' of the multifocal small aperture zone 450 form diffractive focus 550 of 1$^{st}$ order diffraction at Add power from retinal plan 540. The rays 520 and 520' form blur 440 at the retinal plane 540. The size of the blur 440 is determined by a size of the diffractive multifocal small aperture zone 450—smaller zone smaller the blur 440. The smallest size of the zone 450 is the size of two diffractive grooves, groove 1 (central groove) referenced to as 451 and groove 2 (peripheral groove) referenced to as 452. The unexpected outcome of the present invention has been that two grooves with refractive peripheral zone provide remarkable image quality with extended DOF that exceeds the DOF of refractive SAL designs.

The peripheral step 480 can be removed by adjusting the sag of the multifocal small aperture at its periphery—lens thickness adjustment at the central diffractive zone 450, or by adjusting the sag of the refractive peripheral zone 460. A step size is only between 1 and 2 microns and such adjustment does not affect lens 430 optical performance. The sag adjustment leads of "single transition" design of diffractive multifocal small aperture lens as shown on FIG. 9 that leaves only one step 470 for a potential light scattering or irritation of adjacent ocular tissue.

Figure 6:
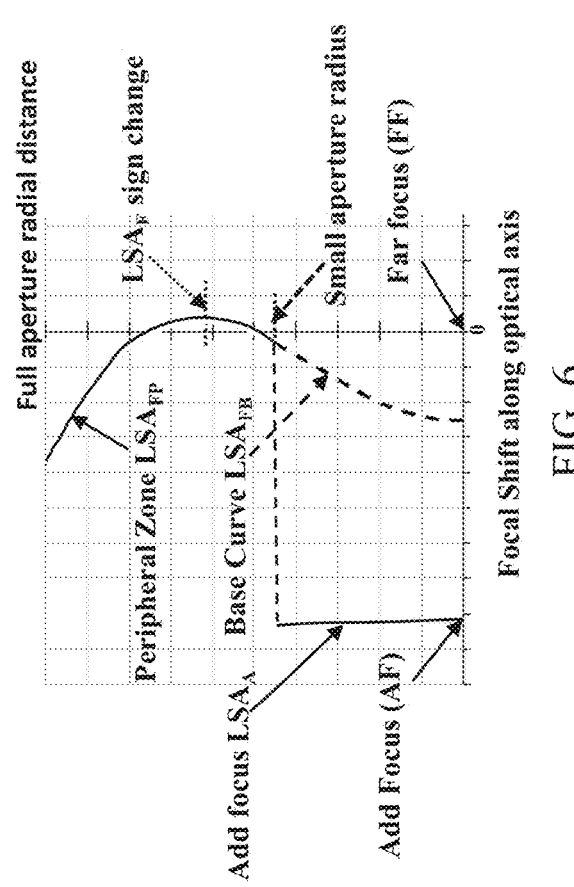
FIG. 6 illustrates optical design in terms of longitudinal spherical aberrations of two virtual lenses that form diffractive small aperture lens. One virtual lens is refractive lens formed by the combination of base curve and peripheral refractive zone shown by far longitudinal spherical aberration $LSA_F$, and another virtual lens is diffractive lens formed by phase coefficients of the of two grooves at Add focus shown by Add longitudinal spherical aberration $LSA_A$.

FIG. 6 demonstrates an example of the optimization of ophthalmic lens design per the present invention on the example of EDOF IVB IOL. Similar optimization can be applied to diffractive multifocal small aperture contact lens, corneal inlay and implantable contact lens. The fundamental principle of diffractive bifocal optic is that it can be represented by two virtual lenses. One is a virtual refractive lens defined by the base curve to form zero-order diffraction allocated to far focus, and another is a virtual diffractive lens defined by diffractive grooves shape to form 1$^{st}$ order diffraction allocated to Add focus. Spherical aberration at far focus $LSA_F$ is a combination of light rays virtually refracted by the base curve to form $LSA_{FB}$ spherical aberration curve within the semi-diameter of the multifocal small aperture, i.e., up to small aperture radius, and light rays refracted by refractive peripheral zone to form $LSA_{FP}$ within the semi-diameter of the full aperture (full aperture radius) and outside small aperture radius, Spherical aberration and Add focus are shown along the horizontal axis representing focal shift along the optical axis where far focus FF position is defined as zero at the axis and Add power at add focus (AF) distance from the far focus. In the optimization of the lens per the present invention, the $LSA_F$ manifests bi-sign aspherical shape to extend DOF around far focus at photopic condition (up to 3 mm pupil) and compensate $LSA_F$ by sign change to reduce spherical aberration contribution on image quality at large pupil (4 to 5 mm pupil) associated with mesopic condition. Spherical aberration $LSA_A$ at add focus formed by the grooves is minimized to concentrate light at Add focus—grooves are designed to form spherical wavefront. This is in order to maximize light concentration at add focus for optimum quality of Add image.

The base curve together with the peripheral refractive zone are defined by standard aspheric format of a refractive aspherical surface:

$$z(r) = \frac{cr^2}{1 + \sqrt{(1 - c^2 r^2)}} + A_4 r^4 + A_6 r^6 + A_8 r^8 + A_{10} r^{10} \tag{4}$$

where z(r)=surface sag; r=distance to the lens center; c=1/R=surface vertex curvature R=surface vertex radius); $A_i$=aspheric coefficients. The following parameters were used for the example of EDOF IVB IOL: R=−18.4 (vertex radius of back convex surface), $A_4$=0.00175, $A_6$=−0.00029, $A_8$=0.00002 and $A_{10}$=−0.0000029.

The grooves phase coefficients to produce certain wavefront shape at Add focus is defined by the phase function:

$$\Phi_{-1}(r) = \frac{2\pi}{\lambda}\left[a_1 r + a_2 r^2 + \ldots + a_n r^n\right] \tag{5}$$

The process is called aspherization of the grooves. The phase coefficients $a_i$ are calculated with the contribution of nominal eye optical system including the base curve contribution to the lens sags to determines aspheric grooves to produce spherical wavefront for minimum spherical aberration at Add focus of Add power of 1.75 D at the (−1)-order of diffraction. The resulted spherical wavefront for Add focus is defined in Zemax optical design software by following non-zero phase coefficients: $a_2$=8.0, $a_4$=1.4 and $a_6$=−0.22. It provides the highest concentration of light at the Add focus allowing to reduce a fraction of light allocated to Add power; (Far:Add) light ratio of the diffraction multifocal zone of EDOF IVB IOL becomes (0.6:0.4) which allows a further reduction in light intensity of the blur at far focus.

Figures 7, 8A, 8B, 8C:
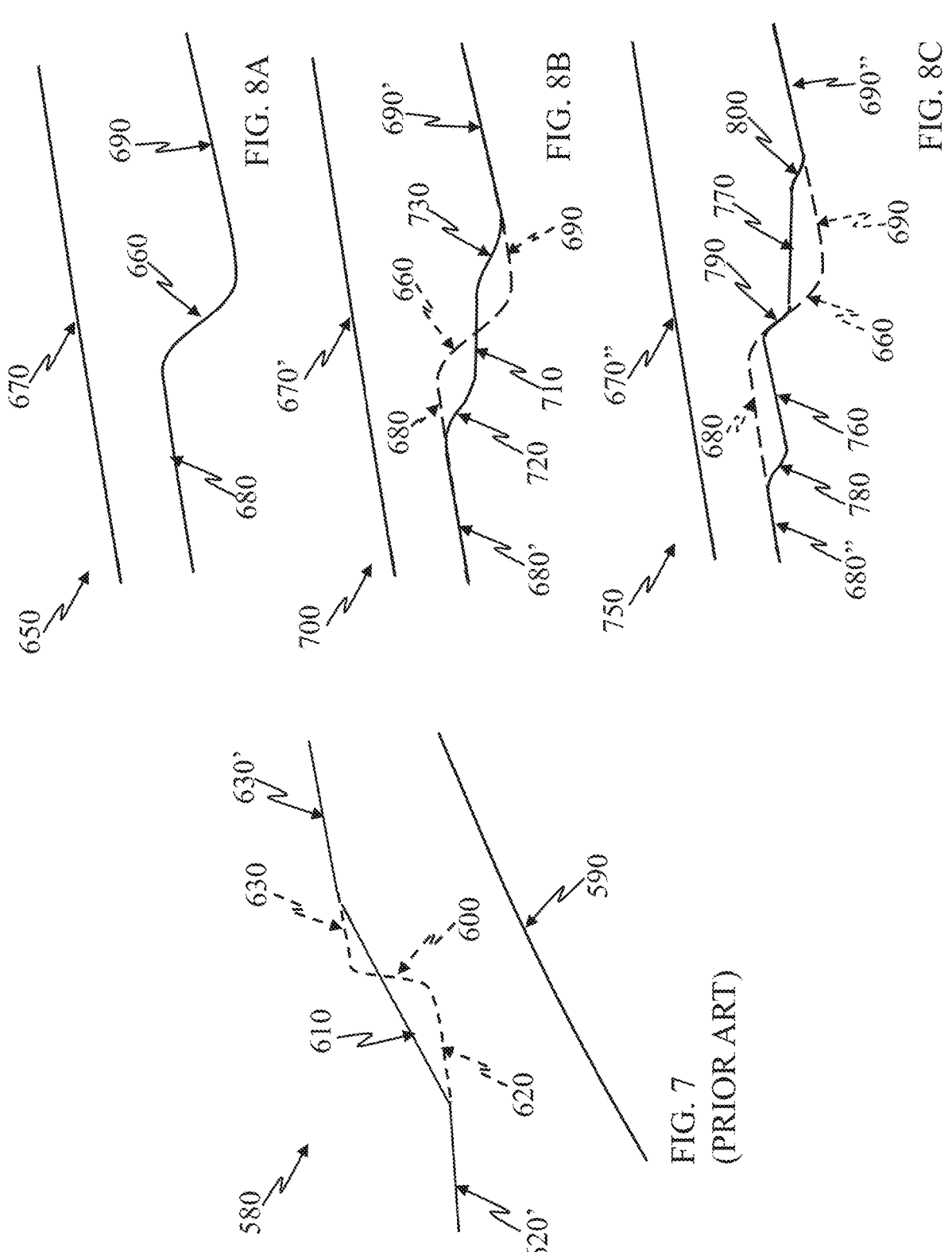
FIG. 7 demonstrates the prior art management of optical step of diffractive multifocal surface by replacing it with refractive sub-zone to refract light to one of the multifocal foci. The technique is dependent upon the base curve shape and periodicity of the diffractive grooves in addition to the optical step height thus limiting its implementation to a narrow range of diffractive surface shapes.
FIGS. 8A, 8B and 8C show modifications of an optical steps of the diffractive surfaces per the present invention that minimizes light scattering off the step and smoothened the diffractive surface to minimize an irritation of adjacent ocular tissue. It is done by dividing an optical step into a set of significantly smaller sub-step and refractive segment that directs light to one of the diffractive multifocal foci.

FIG. 7 demonstrates the prior art management of optical step 460 of diffractive multifocal lens 580 with opposite refractive surface 590 by replacing diffractive surface optical step 600 by refractive sub-zone 610 at the expense of widths of diffractive grooves 620 and 630 which are reduced to the groves 620' and 630'. The shape of the refractive sub-zone 610 is to refract light to one of the diffractive foci of the lens 580. The diffractive lens 580 becomes a combination of diffractive grooves and refractive sub-zones. Fitting sub-zone 610 without substantially reducing the grooves 620' and 630' depends upon base curve shape of the diffractive surface (convex, concave, its steepness), grooves periodicity and step height which limits the technique use to certain diffractive surface configurations such as convex surfaces, for instance.

FIGS. 8A through 8C show modifications of diffractive surface step also into refractive-diffractive form. FIG. 8A shows diffractive lens 650 with original optical step 660 of with opposite surface 670 and diffractive grooves 680 and 690. FIG. 8B shows diffractive lens 700 by the modification of diffractive lens 650 with a transition consisting of one refractive segment 710 and two sub-steps 720 and 730 that converts the original grooves 680 and 690 into grooves 680' and 690'. The lens opposite surface is 670'. The refractive segment 710 is shaped to refract light to one of the diffraction foci of the lens 700. FIG. 8C shows the modification of the diffractive lens 650 into lens 750 by transition consistent of two refractive segments 760 and 770 connected by three sub-steps 780, 790 and 800 that converts the original grooves 680 and 690 into grooves 680" and 690". The lens opposite surface is 670". Each refractive segment 760 or 770 is shaped to refract light to one of the diffractive foci of lens 750.

A selection of a number of segments and sub-steps depends upon a goal of step modification. For instance, to minimize light scattering the sub-step height $H_S < \lambda \cdot n'$, where $\lambda$=blue wavelength of light, say 0.4 micron, and n'=refractive index of surrounding lens media. If original step is height H, then a number of segments is rounded up integer of ratio $H/H_S$ If the objective is to maximize a wear comfort of a contact lens with back diffractive surface, then $H_S$ must be less of a minimum thickness of post-lens tear film thickness (PoLTF) reported as 1 micron in order for sub-zones to be within the minimum PoLTF to minimize a corneal contact by the transition between the grooves. Thus, the smoothened technique of the present invention for the smoothened transition design is to minimize light scattering off a step between the grooves and avoid an irritation of the adjacent ocular tissue by the diffractive surface step without a loss of light outside the diffraction foci.

Figures 9, 10A, 10B:
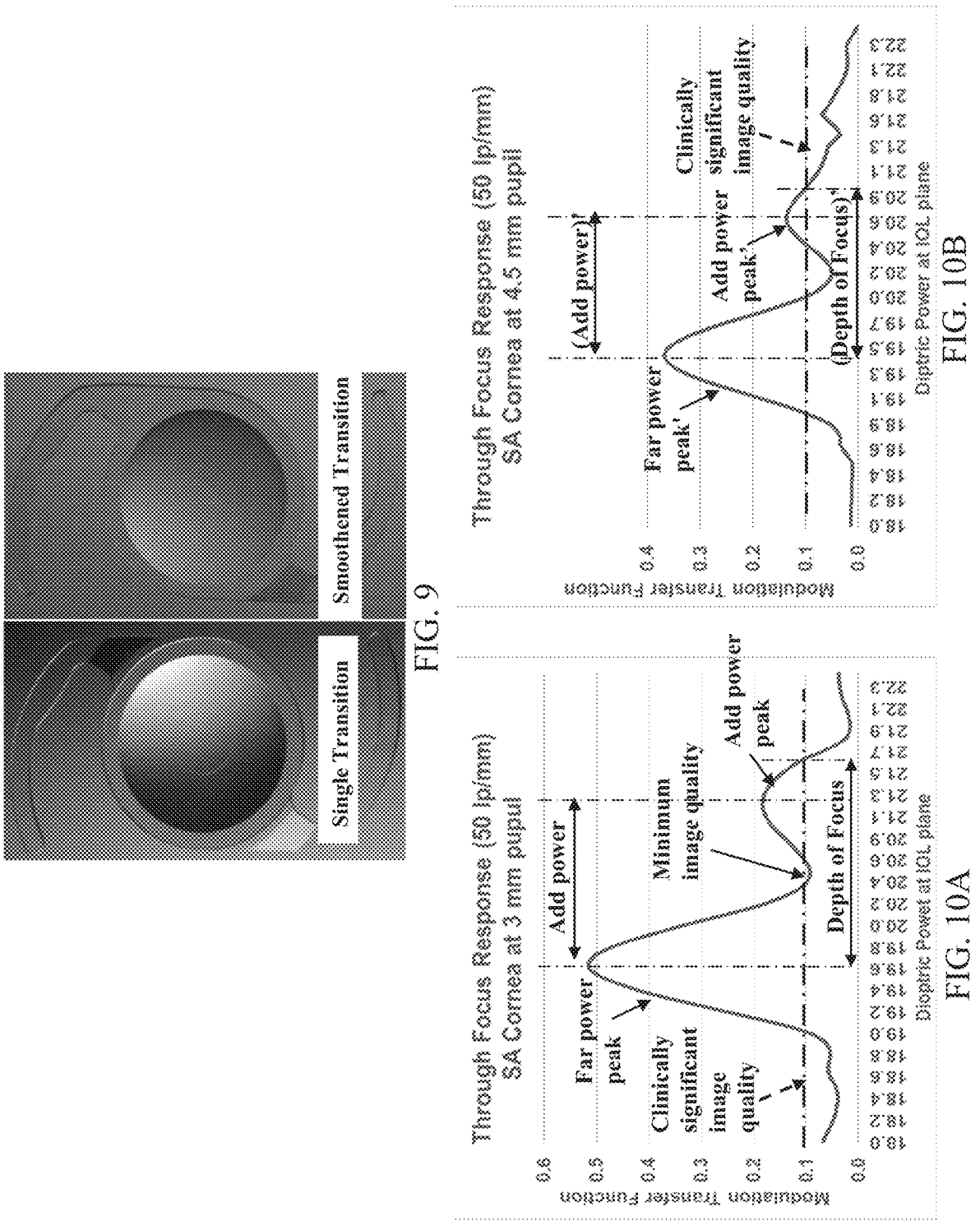
FIG. 9 illustrates diffractive small aperture IOLs per the present invention, one with a single optical step between $1^{st}$ (central) and $2^{nd}$ (peripheral) groove where $2^{nd}$ groove continuous to peripheral refractive zone without a step, so called "single transition" design, and another with further modification of single transition design by smoothened the remaining optical step by the technique described in the FIG. 8C, so called "smoothened transition" design.
FIGS. 10A and 10B demonstrate in-vitro measurement for Through Focus Responses at 50 lp/mm of diffraction multifocal small aperture IOL per the present invention and called EDOF IVB IOL. It includes smoothened transition design called EDOF IVB IOL. It was tested in SA nominal Eye Model at 3 mm pupil diameter representing photopic condition and 4.5 mm pupil diameter representing mesopic condition.

FIG. 9 demonstrates photos of the EDOF IVB IOL in two designs—one visible central step between central and peripheral grooves with a smooth transition between peripheral groove and peripheral refractive zone, so called "single transitional" design, and another is further modification of single transition design by smoothened central step per the technique described in FIG. 8C, so called "smoothened transition" design.

FIGS. 10A and 10B show optical test results of EDOF IVB IOL with smoothened transition design by Trioptics Optispheric IOL PRO 2 optical bench for Through Focus Response (TFR) defined as MTF measurement at 50 lp/mm spatial frequency taken at different dioptric powers. TFR is in-vitro measurement of image contrast and selected spatial frequency corresponds to 20/40 Snellen visual acuity commonly used in clinical trials for vision quality measure. The testing was conducted per ISO specifications with SA corneal lens representing nominal human cornea and 3 mm pupil (FIG. 10A) associated with photopic condition and 4.5 mm pupil (FIG. 10B) associated with mesopic condition.

In-vitro MTF(50 lp/m) at 3 mm manifest Multipeak performance with far power peak of 0.53 and Add power peak of 0.2 level separated by Add power=1.75 D in IOL plane. The MTF(50 lp/mm)=0.53 represents excellent image quality corresponding to monofocal IOL image quality close to 4 mm pupil which clinically commonly occurs and has not been reported of any visual issue. The MTF(50 lp/mm)=0.1 represents clinically significant image quality meaning that a patient with the lens reaching MTF(50 lp/mm)=0.1 is expected also to reach 20/40 visual acuity. The optimum design of EDOF IVB IOL demonstrates that minimum image quality between the far and Add peaks is close to clinically significant image quality defined as 0.1. It leads to continue DOF at 3 mm pupil of 2 D, i.e., the expected vision range of 20/40 or better visual acuity from far distance to about 50 cm from the eye.

According to FIG. 10B, far image quality at 4.5 mm pupil is also of remarkable level and the TFR also manifests Add focus peak above MTF(50 lp/mm)=0.1. Similar outcomes were recorded with diffractive small aperture contact lens testing. The FIGS. 10A and 10B demonstrate excellent far image quality even at low light condition (4.5 mm pupil) and significantly extended DOF over refractive small aperture ophthalmic lenses and pinhole ophthalmic lenses. Such remarkable optical test outcomes manifested by diffractive small aperture ophthalmic lenses as shown on the example of EDOF IVB IOL per FIGS. 10A and 10B were unexpected and lead to the analysis of imaging capability of such optic and the development of a design method for small aperture ophthalmic lens design that meets the requirements for halo reduction, significantly extended DOF and excellent far image quality.

FIG. 11 demonstrates theoretical TFR(50 lp/m) of diffractive multifocal small aperture lens (EDOF IVB IOL) in SA Eye Model (nominal corneal lens). The setting is equivalent to in-vitro testing of the FIG. 10A. The horizontal axis is focal shift in millimeters in place of dioptric power used in-vitro testing and as result, the Add focus peak in FIG. 11 is in opposite side from far focus peak as compared in FIG. 10A. Similar to TFR in FIG. 10A, the theoretical TFR(50 lp/mm) of the EDOF IVB IOL demonstrates Multipeak performance of the diffractive multifocal small aperture lens characterized by Add Power=1.75 D and $DOF_D$=2 D as measured in dioptric power. As above, DOF is measured as TFR(50 lp/mm) range not less than 0.1 modulation which defines clinically significance image quality.

The FIG. 11 also includes TFR(50 lp/mm) of the refractive multifocal small aperture IOL in the same SA Eye Model at 3 mm pupil. Refractive multifocal central zone has the same zone diameter as diffractive multifocal central zone of 2.3 mm. It is of zonal design to equally split light between two foci also separated by 1.75 D to match AP of diffractive multifocal small aperture lens, i.e., is has central and peripheral sub-zones of equal areas to refract light to far focus (0.0 mm) and the focus located at 1.75 D from far focus. The sub-zones as well as peripheral zone of far focus were aspherized to maximizer light concentration at far focus and Add focus at 1.75 D. The refractive design was the closet design in terms of light distribution to the diffractive design to allow for the best comparison of both multifocal small aperture designs. Despite light concentration to two foci the theoretical refractive small aperture lens TFR(50 lp/mm) manifests Unipeak performance of broad but single peak centered at far focus with $DOF_R \approx 1.7$ D. Noticeably, far image quality of refractive SAL is lower the one by diffractive SAL. The theoretical comparison between diffraction SAL and refractive SAL largely confirmed the observations of the in-vitro optical testing and outcomes of the clinical trials. Thus, the Multipeak performance is superior of Unipeak performance in terms of far image quality and DOF for the same small aperture size, very similar light split between foci and focusing to the foci of same Add power.

FIG. 12 explains the forming Multipeak and Unipeak performances demonstrated in FIG. 11 and illustrates the design method to provide a Multipeak performance by a multifocal small aperture lens and even for any type of multifocal lens. The illustration of the method employs the example of the diffractive SAL and refractive SAL of the FIG. 11. The method consists of the following steps. Each of diffractive and refractive lenses is bifocal lens and can be represented by two virtual monofocal lenses that focus light at far and Add foci. The method is based on the determination of TFR at a selected spatial frequency, say 50 lp/mm, and the TFR(50 lp/m) is taken of each virtual lens. In case of diffractive SAL, one virtual lens is refractive lens which TFR forms zero-order far peak and another virtual diffractive lens which TFR forms first-order Add peak. Refractive SAL is also represented by two virtual lenses, one virtual lens includes lens areas of far power and its TFR forms far zone peak and another virtual lens consists of the area of Add power and its TFR forms Add zone peak. Clinically significant image quality is replaced by "uni-multi band" of 0.05 modulation range above clinically significant image quality level. Commonly, clinically significant image quality is 0.1 modulation as shown on the FIG. 11 but it could be different in the method application. The method states that TFR of the multifocal lens that combines virtual two monofocal lenses of far and Add foci manifest Unipeak performance if its TFRs of the minimum overlap of virtual lenses focal peaks is above uni-multi band or Multipeak performance if the minimum overlap of virtual lenses focal peaks is below the uni-multi band. Per FIG. 12, the minimum overlap(R) of refractive multifocal small aperture IOL is above the uni-multi band resulting in Unipeak performance shown in FIG. 11, the minimum overlap(D) of the diffractive multifocal small aperture IOL is below the uni-multi bank resulting in Multipeak performance in FIG. 11. Thus, the method guides a selection of different combination of multifocal zone diameter, Add power or optical design of a virtual lens to change width of one or both TFRs of the virtual lenses to convert Unipeak performance into Multipeak performance or vice versa.

Physical explanation of the observation is that the overlap between TFRs of virtual lenses represents a level of light interference between light beams at each focus that are directed to different foci. For instance, TFR of far zone peak of refractive small aperture lens is very broad because of its small central sub-zone diameter producing pinhole effect. The corresponding beam of light is still of a concentrated intensity at Add focus thus suppressing a quality of image produced by add focus virtual lens of the refractive small aperture lens. With its low Add zone peak produced by sub-zone of ring-shape to start with, the Add zone peak at add focus is totally suppressed in the combined TFR of the refractive small aperture lens thus resulting in Unipeak performance with TFR peak centered at far focus. Virtual lenses of diffractive small aperture lens despite similar light split, both have the same clear aperture defined by the central multifocal zone size and, as a result, each produces a relatively narrow and high image peak (Add focus peak and far focus peak) with very small overlap for selected Add power and multifocal zone size. As a result, the interference between light beams at each focus is limited resulting in TFR of Multipeak performance for the diffractive small aperture lens.

It has been a common acceptance of diffractive optic benefit for full aperture ophthalmic lens with its ability to maintain image quality at different foci with a change of eye pupil. The method explains the benefit of diffractive optic for small aperture ophthalmic lens where a change in eye pupil is not a consideration. The benefit of diffractive optic lies with its ability to produce Multipeak performance of superior DOF and far image quality at small size of central multifocal zone necessary in managing halos.

FIGS. 13A through 13D compare responsible for halos out-of-focus blurs at far foci of the diffractive multifocal small aperture IOL and refractive multifocal small aperture IOL analyzed in FIG. 12 using spot diagrams, i.e., images of a point source. FIGS. 13A and 13B show diffractive SAL in-focus image 820 and blur 810 at 3 mm pupil and in-focus image 830 and blur 810 at 4.5 mm pupil. Due to small aperture design with small multifocal zone, the blur at far is pupil independent, i.e., small blur size and intensity is maintained at large pupil occurred at low light condition thus making halos les visible. FIGS. 13C and 13D shows refractive SAL in-focus image 850 and blur 840 at 3 mm pupil and in-focus image 860 and blur 840 at 4.5 mm pupil. Similar to diffractive design, the blur is also pupil independent due to small aperture design.

A comparison of blur 810 of the diffractive multifocal SAL and blur 840 of refractive multifocal SAL demonstrates another potential benefit of diffractive optic. Light distribution at blur 810 is uniform as the clear aperture of add focus virtual lens equals central multifocal zone size. Light distribution of the refractive multifocal SAL blur 840 is not uniform due to ring-shape of clear aperture the add focus virtual lens thus creating an area of higher light intensity that potentially becomes more visible as halos.

Referring in general to the present invention disclosed in this application, by referencing to a diffractive multifocal lens with a far and an Add foci, it applies automatically that it would be at least two grooves. A reason for a 2.5 mm limit is that it falls under the definition known to those skilled in the art of a "small aperture lens," meaning that such a multifocal diameter does not depend upon lighting condition as the nominal eye pupil is 2.5 mm for elderly patients at daytime lighting and the pupil is higher in low lighting, thus full multifocal zone is always exposed.

On the other hand, if the multifocal zone is too small, the peaks from virtual lenses are broadened too much. From our findings, it has appeared that diffractive multifocal zone has to be as small as possible to minimize halos (this is defined by the minimum number of grooves, which is two) but not too small where only a small fraction of light is reaching an Add focus at the nominal eye pupil and also to avoid a strong pinhole effect when light beam formed by the pinhole at the Add focus is of extended depth of focus and thus interferes with light beam focused at far focus which likely leads to unipeak performance. Therefore, there is also the minimum multifocal zone size of about 1.5 millimeters.

The Applicant teaches that at least 20% of light directed within the diffractive multifocal zone of the transmissive ophthalmic lens is to one of the far and the Add focus. In regard to the 20%, it refers to a fraction of light produced by the diffractive multifocal zone, not including the peripheral zone, where light is split by the diffractive multifocal zone. The central characteristic of a diffractive optic is that the grooves are working together to produce constructive interference at certain points called diffraction orders. The height (step height) controls how light is split between these diffraction orders. One skilled in the art can choose one diffractive order, say zero order, as the far focus and another, say 1st order, as the Add focus. The positions of the diffractive orders depend upon periodicity of the grooves—wider widths of grooves (lower periodicity) produce larger separation between foci, i.e., Low Add power (as Surface B in FIG. 2) and narrower widths of grooves (high periodicity) produce narrower separation between foci, i.e., high Add power (as Surface A in FIG. 2). At a certain step height, we may have at least 20% of light focused at the far focus to produce a minimum image intensity needed to be able to see a far object, then about 65% is then directed to Add focus where the rest of light is split between higher diffraction orders due to the nature of a diffractive optic. Those skilled in the art can select a different step height to direct at least 20% of light focused at the Add focus to create adequate light intensity image of closer to the eye object at the Add focus at the retina.

What is claimed is:

1. A transmissive ophthalmic lens, comprising:
a first surface opposite a second surface;
the first surface comprising a centrally disposed diffractive multifocal zone surrounded by a peripherally disposed refractive non-multifocal zone;
the second surface being a refractive non-multifocal surface;
wherein the diffractive multifocal zone is no more than 2.5 millimeters configured to mitigate halos and no less than 1.5 mm diameters configured for the transmissive ophthalmic lens to manifest multipeak performance with a far focus and an Add focus;
wherein at least 20% of light directed within the diffractive multifocal zone of the transmissive ophthalmic lens is to one of the far and the Add focus;
wherein the refractive non-multifocal zone is configured to form the far focus; and
wherein a smoothened transition is disposed between two consecutive grooves, wherein the smoothened transition includes a refractive segment connected to each groove by a step.

2. The lens of claim 1, wherein a first groove and a second groove of the diffractive multifocal zone are the only two grooves.

3. The lens of claim 2, wherein a transition is disposed between the first groove and the second groove, wherein the transition includes a refractive segment connected to each groove by a step.

4. The lens of claim 1, wherein the non-multifocal refractive surface of the second surface is spherical, aspheric or cylinder.

5. The lens of claim 1, wherein the transmissive ophthalmic lens is an intra-ocular lens.

6. The lens of claim 1, wherein the transmissive ophthalmic lens is an implantable contact lens.

7. The lens of claim 1, wherein the transmissive ophthalmic lens is a corneal inlay lens.

8. The lens of claim 1, wherein the transmissive ophthalmic lens is a contact lens.

9. The lens of claim 1, wherein the diffractive multifocal zone comprises a base curve together with the refractive non-multifocal zone that is bi-sign aspheric.

10. The lens of claim 1, wherein the diffractive multifocal zone includes high periodicity structure and low periodicity structure synchronized with each other that each width of low periodicity structure includes two widths of high periodicity structure.

11. The lens of claim 1, wherein the diffractive multifocal zone includes not more than two grooves of low periodicity structure each consisting of two widths of high periodicity structure.

12. The lens of claim 1, wherein the diffractive multifocal zone is configured to manifest a multipeak performance with the Add power of 1.75±0.5 D.

13. A transmissive ophthalmic lens, comprising:
a first surface opposite a second surface;
the first surface comprising a centrally disposed diffractive multifocal zone surrounded by a peripherally disposed refractive non-multifocal zone;
the second surface being a refractive non-multifocal surface;
wherein the diffractive multifocal zone is no more than 2.5 millimeters configured to mitigate halos and no less than 1.5 mm diameters configured for the transmissive ophthalmic lens to manifest multipeak performance with a far focus and an Add focus;
wherein a first groove and a second groove of the diffractive multifocal zone are the only two grooves;
wherein at least 20% of light directed within the diffractive multifocal zone is to one of the far and the Add focus;
including a smoothened transition disposed between the first groove and the second groove that includes a refractive segment connected to each groove by a step; and
wherein the refractive non-multifocal zone is configured to form the far focus.

14. A transmissive ophthalmic lens, comprising:
a first surface opposite a second surface;
the first surface comprising a centrally disposed diffractive multifocal zone surrounded by a peripherally disposed refractive non-multifocal zone;
the second surface being a refractive non-multifocal surface;
wherein the diffractive multifocal zone is no more than 2.5 millimeters configured to mitigate halos and no less than 1.5 mm diameters configured for the transmissive ophthalmic lens to manifest multipeak performance with a far focus and an Add focus;
wherein at least 20% of light directed within the diffractive multifocal zone is to one of the far and the Add focus;
wherein the diffractive multifocal zone includes not more than two grooves of low periodicity structure each consisting of two widths of high periodicity structure; and
wherein the refractive non-multifocal zone is configured to form the far focus.

* * * * *